United States Patent
Baumann et al.

(10) Patent No.: US 7,211,615 B2
(45) Date of Patent: May 1, 2007

(54) POLYAMIDE POWDER WITH LONG-LASTING, CONSISTENTLY GOOD FLOWABILITY

(75) Inventors: Franz-Erich Baumann, Duelmen (DE); Sylvia Monsheimer, Haltern am See (DE); Maik Grebe, Bochum (DE); Wolfgang Christoph, Marl (DE); Dirk Heinrich, Herten (DE); Holger Renners, Velen (DE); Heinz Scholten, Haltern am See (DE); Thomas Schiffer, Haltern am See (DE); Joachim Muegge, Haltern am See (DE); Johannes Chiovaro, Marl (DE)

(73) Assignee: Degussa AG, Düsseldorf (DE)

( * ) Notice: Subject to any disclaimer, the term of this patent is extended or adjusted under 35 U.S.C. 154(b) by 403 days.

(21) Appl. No.: 10/700,535

(22) Filed: Nov. 5, 2003

(65) Prior Publication Data
US 2004/0204531 A1    Oct. 14, 2004

(30) Foreign Application Priority Data
Nov. 7, 2002    (DE) ............................. 102 51 790

(51) Int. Cl.
 C08J 3/00    (2006.01)
 C08K 3/34    (2006.01)
 C08L 67/00    (2006.01)
 C08G 63/60    (2006.01)
 A61K 6/00    (2006.01)

(52) U.S. Cl. .............. 524/492; 264/497; 264/652; 264/126; 424/401; 424/489; 424/497; 427/459; 427/461; 427/474; 427/475; 427/485; 427/508; 427/133; 427/185; 427/195; 524/493; 524/599; 524/602; 524/606; 524/607

(58) Field of Classification Search ................ 524/492, 524/493, 599, 602, 606, 607; 264/497, 652; 264/126; 424/401, 489, 497, 501; 427/459, 427/461, 474, 475, 485, 508, 133, 185, 195
See application file for complete search history.

(56) References Cited

U.S. PATENT DOCUMENTS

| | | | |
|---|---|---|---|
| 2,811,499 A | 10/1957 | Hervey | |
| 3,864,432 A | 2/1975 | Adler et al. | |
| 4,334,056 A | 6/1982 | Meyer et al. | |
| 5,405,936 A | 4/1995 | Mumcu et al. | |
| 5,424,161 A * | 6/1995 | Hayashi et al. | 430/108.3 |
| 5,668,242 A | 9/1997 | Simon et al. | |
| 5,898,043 A * | 4/1999 | Uemae et al. | 523/204 |
| 5,932,687 A | 8/1999 | Baumann et al. | |
| 6,060,550 A | 5/2000 | Simon et al. | |
| 6,110,411 A * | 8/2000 | Clausen et al. | 264/497 |
| 6,149,836 A | 11/2000 | Mumcu et al. | |
| 6,207,768 B1 * | 3/2001 | Sato et al. | 525/438 |
| 6,300,413 B1 | 10/2001 | Simon et al. | |
| 6,316,537 B1 | 11/2001 | Baumann et al. | |
| 6,335,101 B1 | 1/2002 | Haeger et al. | |
| 6,379,856 B2 * | 4/2002 | Sokol et al. | 430/108.24 |
| 6,403,851 B1 | 6/2002 | Wilczock et al. | |
| 6,407,304 B2 | 6/2002 | Schiffer et al. | |
| 6,444,855 B1 | 9/2002 | Esser et al. | |
| 6,462,235 B1 | 10/2002 | Thiele et al. | |
| 6,521,290 B1 * | 2/2003 | Kudo et al. | 427/214 |
| 6,566,555 B2 | 5/2003 | Thiele et al. | |
| 6,579,581 B2 | 6/2003 | Bartz et al. | |
| 6,589,606 B2 | 7/2003 | Waterkamp et al. | |
| 6,610,864 B2 | 8/2003 | Krebs et al. | |
| 6,620,970 B2 | 9/2003 | Schiffer et al. | |
| 6,639,108 B2 | 10/2003 | Schiffer et al. | |
| 6,656,997 B2 | 12/2003 | Baumann et al. | |
| 6,664,423 B2 | 12/2003 | Herwig et al. | |
| 6,677,015 B2 | 1/2004 | Himmelmann et al. | |
| 6,766,091 B2 | 7/2004 | Beuth et al. | |
| 6,784,227 B2 | 8/2004 | Simon et al. | |
| 6,852,893 B2 | 2/2005 | Kuhnle et al. | |
| 6,855,759 B2 * | 2/2005 | Kudo et al. | 524/261 |
| 6,884,485 B2 | 4/2005 | Baumann et al. | |
| 2003/0124281 A1 | 7/2003 | Ries et al. | |
| 2004/0009340 A1 * | 1/2004 | Zhu et al. | 428/323 |
| 2004/0086735 A1 | 5/2004 | Monsheimer et al. | |
| 2004/0097636 A1 | 5/2004 | Baumann et al. | |
| 2004/0106691 A1 | 6/2004 | Monsheimer et al. | |
| 2004/0137228 A1 | 7/2004 | Monsheimer et al. | |
| 2004/0140668 A1 | 7/2004 | Monsheimer et al. | |
| 2004/0180980 A1 | 9/2004 | Petter et al. | |
| 2004/0204531 A1 | 10/2004 | Baumann et al. | |

(Continued)

FOREIGN PATENT DOCUMENTS

DE    2817027    *   7/1979

(Continued)

OTHER PUBLICATIONS

Petrovicova, et al., "Nylon 11/Silica Nanocomposite Coatings Applied by the HVOF Process. I. Microstructure and Morphology", Journal of Applied Polymer Science, vol. 77, 2000, pp. 1684-1699.

(Continued)

Primary Examiner—Patrick D. Niland
(74) Attorney, Agent, or Firm—Oblon, Spivak, McClelland, Maier & Neustadt, P.C.

(57) ABSTRACT

A composition containing from 88 to 99.99% by weight of a polyamide, a compound of a polyamide and mixtures of these, and from 0.01 to 0.25% by weight of a flow aid where the drying loss from the flow aid after 5 days of conditioning at a relative humidity of 95% is less than or equal to 1%, determined by ISO 787/2.

20 Claims, No Drawings

U.S. PATENT DOCUMENTS

| | | | |
|---|---|---|---|
| 2004/0206443 | A1 | 10/2004 | Monsheimer et al. |
| 2004/0232583 | A1 | 11/2004 | Monsheimer et al. |
| 2005/0014842 | A1 | 1/2005 | Baumann et al. |
| 2005/0027047 | A1 | 2/2005 | Monsheimer et al. |
| 2005/0027050 | A1 | 2/2005 | Monsheimer et al. |
| 2005/0038201 | A1 | 2/2005 | Wursche et al. |

FOREIGN PATENT DOCUMENTS

| | | |
|---|---|---|
| DE | 31 13 392 A1 | 12/1982 |
| EP | 0 004 859 | 10/1979 |

OTHER PUBLICATIONS

Petrovicova, et al., "Nylon 11/Silica Nanocomposite Coatings Applied by the HVOF Process. II. Mechanical and Barrier Properties", Journal of Applied Polymer Science, vol. 78, 2000, pp. 2272-2289.

U.S. Appl. No. 11/484,593, filed Jul. 12, 2006, Monsheimer, et al.
U.S. Appl. No. 11/480,459, filed Jul. 5, 2006, Dowe et al.
U.S. Appl. No. 10/685,525, filed Oct. 16, 2003, Baumann et al.
U.S. Appl. No. 10/700,535, filed Nov. 5, 2003, Baumann et al.
U.S. Appl. No. 10/637,613, filed Aug. 11, 2003, Monsheimer et al.
U.S. Appl. No. 10/317,122, filed Dec. 12, 2002, Schiffer et al.
U.S. Appl. No. 10/407,167, filed Apr. 7, 2003, Waterkamp et al.
U.S. Appl. No. 11/293,360, filed Dec. 5, 2005, Monsheimer et al.
U.S. Appl. No. 11/241,667, filed Oct. 3, 2005, Monsheimer et al.
U.S. Appl. No. 11/356,416, filed Feb. 17, 2006, Monsheimer et al.
U.S. Appl. No. 11/335,587, filed Jan. 20, 2006, Monsheimer.
U.S. Appl. No. 11/271,847, filed Nov. 14, 2005, Franz et al.
U.S. Appl. No. 11/354,114, filed Feb. 15, 2006, Dowe et al.
U.S. Appl. No. 11/354,100, filed Feb. 15, 2006, Dowe et al.

* cited by examiner

US 7,211,615 B2

POLYAMIDE POWDER WITH LONG-LASTING, CONSISTENTLY GOOD FLOWABILITY

BACKGROUND OF THE INVENTION

1. Field of the Invention

The invention relates to a composition which has long-lasting and consistently good flowability and comprises a polyamide powder and a flow aid. The composition can be used for coating moldings or for the production of test specimens by laser-sintering. The composition may also be used in the production of cosmetics or coating materials.

2. Description of the Background

Polyamide powders are widely used in industry, e.g. for coating metal parts, as additives in coating materials and cosmetics, and also for the production of test specimens or small runs by rapid-prototyping using selective laser sintering. High requirements are placed upon the processability of the powders used in these applications. A particularly critical parameter of the polyamide powder is flowability. Caking within polyamide powders can lead to inhomogeneity in the resultant coating or in the test specimen. Powders must retain good flowability whatever the storage conditions, such as unopened or opened packs. Specifically in the case of opened packs, consistent processability has to be ensured irrespective of the atmospheric conditions prevailing during storage, e.g. temperature and variations in humidity.

Polyamide powders absorb water by way of hydrophilic carboxamide groups. There is a relationship between the chain lengths of the monomers used to form the polyamide and the water absorption of the resultant polyamide. For example, powders based on nylon-11 and nylon-12 have lower water absorption since they have fewer carboxamide group based on the methylene groups in the polymer, than polyamides prepared from shorter-chain monomers. Water absorption in polyamide powders leads to caking which results in poor flowability. Caking is particularly pronounced with polyamide powders produced by milling. Poor flowability in polyamide powder is accompanied by poor processability.

U.S. Pat. No. 4,334,056 describes a process for producing pulverulent coating agents based on polyamides having at least 10 aliphatically bonded carbon atoms per carboxamide group. The coating agents produced by that process can be used to produce lacquer-like coatings on metals. The methods used for this coating include fluidized-bed sintering, flame-spraying and electrostatic coating. When heated to temperatures near the film-forming temperature, the coating compositions produced by this process form coatings with a smooth surface, good edge coating, good elasticity, and excellent resistance to aqueous alkalis, with no formation of undesirable fumes. The coating powders produced in U.S. Pat. No. 4,4334,056 have a defined particle size distribution which is determined by the production conditions. The flowability of the resultant polyamides is adequate immediately after production. As is the case with prior-art polyamide powders, when the powders produced by this process are stored at varying humidity and temperature their flowability suffers due to caking.

DE 31 13 392 discloses a process for reducing the electrostatic charging of pulverulent thermoplastic polyamides. The coating powder produced from thermoplastics using this process contains small amounts of a finely divided inorganic powder which has been coated with an antistat, together with pulverulent thermoplastic polyamides. Organic ammonium compounds or organic amine compounds are present as an antistat. The amount of resultant coated powder added is from 0.01 to 0.03 part by weight, based on 100 parts by weight of polyamide. The resultant modified polyamide powder has better fluidizability in fluidized-bed sintering when compared with an unmodified powder. However, DE 31 13 392 gives no information as to whether the coating powder described retains its flowability, and thus its suitability as a coating powder, after storage at varying temperature and humidity. Since the antistat coating is hydrophilic, it may be assumed that the flowability of the coating composition is reduced on storage at varying temperature or humidity.

Petrovicova et al. [J. Appl. Polym. Sc. 77 (2000) 1684–1699; ibid. 78 (2000) 2272–2289] describe a high-velocity oxyfuel process (HVOF process). In the HVOF process a polymer powder is provided with pigments to improve the properties of the coating layer. The powder composition is used for coating metal parts. The polymer powder is melted by means of a combustion spray gun and, while molten, applied to the material to be coated. Petrovicova investigated the effect of hydrophilic silicas, hydrophobic silicas, carbon black or A 1100 γ-aminopropyltriethoxysilane-modified silica as pigments in the mixture with nylon-11 on the properties of the resultant coatings. For this, 5, 10, 15 and 20% by volume of the pigment were added to the nylon-11. This corresponds to a proportion of from 0.3 to 3% by weight of pigment in the coating composition. The respective pigment and nylon-11 are mixed and milled for 48 h in a mill which comprises zirconia beads as a milling aid. The long milling time incorporates the pigment very homogeneously into the nylon-11 grains. Petrovicova found that the properties of the resultant coating are dependent on the proportion of pigment. The highest strength properties of the resultant coating are achieved with 20% of pigment by volume in the coating composition. Neither of the documents describes improvement of the flowability of the coating composition due to the pigments used. Nor is there any indication to the skilled worker of the effect of the pigments disclosed on the flowability of the coating composition.

SUMMARY OF THE INVENTION

Accordingly, it is an object of the present invention to provide a composition comprising a polyamide, derivatives of polyamides, or a mixture of these, which, irrespective of the storage conditions for the composition, assures consistent flowability and processability. Irrespective of the storage conditions, in particular when there are temperature variations or humidity variations, the composition is intended to be useful with consistent quality for coating moldings, for production of test specimens by laser-sintering, for the production of cosmetics and for the production of coating materials.

DESCRIPTION OF THE PREFERRED EMBODIMENTS

This object is achieved by a composition comprising from 88 to 99.99% by weight of a polymer selected from the group polyamides, derivatives of polyamides, and mixtures of these, and from 0.01 to 0.25% by weight of a flow aid, where the drying loss from the flow aid after 5 days of conditioning at relative humidity of 95% is less than or equal to 1% by weight, determined to ISO 787/2. From 0 to 11.99% by weight of one or more conventional additives may optionally also be present in the composition.

Unexpectedly, when polyamides, which are by nature hydrophilic, are combined with flow aids selected in this manner, they exhibit good flowability irrespective of the storage conditions. A flow aid with a drying loss less than or equal to 1% after 5 days of conditioning at relative humidity of 95% is itself capable of absorbing no, or only very little, water or water vapor from the environment. The flow aid is not therefore acting as a drying agent in the composition, and cannot therefore reduce the water absorption of the polyamide. The skilled worker would assume that the polyamide in the composition of the invention would then absorb water or water vapor from the surrounding air and thus cake. Surprisingly, this expected caking of the polyamide is not observed in the case of the composition of the invention.

The polymer is preferably selected from the group including nylon-12, nylon-11, nylon-6,10, nylon 6,12, nylon-10,12, nylon-6, nylon-6,6, and mixtures of these. The amount of the polymer present in the composition is preferably 95 to 99.99% by weight, in particular from 97 to 99.99% by weight, more preferably from 99.0 to 99.99% by weight, still more preferably from 99.5 to 99.99% by weight, in particular from 99.75 to 99.99% by weight, and particularly preferably from 99.8 to 99.99% by weight. In another preferred embodiment, the amount of the polymer present in the composition is from 99.82 to 99.99% by weight, in particular from 99.85 to 99.99% by weight, more preferably from 99.88 to 99.99% by weight, and particularly preferably from 99.9 to 99.99% by weight.

Derivatives of polyamides include compounds of polyamides such as blends of polyamides with an additional resin, for example polyamide/epoxy and polyamide/polyvinyl alcohol blends obtained by extruding a mixture of the polyamide and the polyvinylalcohol or epoxy. Such compounds may contain from 1 to 20% by weight of the additional polymer based on the weight of the compound of polyamide. Powders of such compounds of polyamide may be obtained by, for example, freeze grinding. When a derivative of polyamide is used in the invention the amount by weight of the derivative is based on the sum of the weights of the polyamide and the additional resin.

In one preferred embodiment, the flow aids are selected from the group including inorganic pigment, silica, fumed silica, precipitated silica, colloidal silica, hydrophobized silica, hydrophobic silica and mixtures of these. The amount of the flow aid present in the composition is preferably from 0.01 to 0.2% by weight, in particular from 0.01 to 0.18% by weight, more preferably from 0.01 to 0.15% by weight, still more preferably from 0.01 to 0.12% by weight, and particularly preferably from 0.01 to 0.1% by weight.

The hydrophobic or hydrophobized silica is preferably obtained by reacting silica with a hydrophobicizer. The hydrophobicization preferably takes place after precipitation or pyrolysis of the silica, and via substantial reaction of free OH groups of the silica with, for example, silanes, silazanes, or siloxanes. Preferred hydrophobicizers are hexadecylsilane, dimethyldichlorosilane, hexamethyldisilazane, octamethylcylcotetrasiloxane, polydimethylsiloxane or methacrylic silanes.

The polymer used has a median particle size ($d_{50}$) of from 0.1 to 250 μm, preferably from 1 to 150 μm, particularly preferably from 1 to 120 μm, and more preferably from 5 to 80 μm.

Flow aids are generally composed of nano-scale primary particles. For example, commercially available Aerosils have a primary particle size of a few nanometers (e.g. from 7 to 12 nm). The primary particles usually form larger agglomerates or aggregates. When the flow aid is incorporated in the polymer powder by mixing, the agglomerates or aggregates are only partially broken down, and the function of the flow aid is therefore exerted not only by individual nano-scale primary particles but also by the agglomerates and aggregates. When the median particle size of the flow aid is determined, individual primary particles are usually found together with aggregates and agglomerates.

The flow aid of the invention has a median particle size of from 5 nm to 200 μm. The preferred median particle size of the flow aid is from 10 nm to 150 μm, particularly preferably from 100 nm to 100 μm.

The flow aid has a specific surface area of from 20 to 600 $m^2/g$. The flow aid preferably has a specific surface area of from 40 to 550 $m^2/g$, particularly preferably from 60 to 500 $m^2/g$, and more preferably from 60 to 450 $m^2/g$.

The optional additive, which is not a flow aid, is an additive whose use is conventional. It can be selected from the group consisting of one or more of metal powders, ferrites, organic color pigment, inorganic color pigment, carbon black, uncolored organic filler, uncolored inorganic filler, amorphous or semicystalcine filler, supercooled melts, pH regulators, and mixtures of these. In one preferred embodiment, the additive is aluminum powder, barium sulfate, titanium dioxide, zirconium dioxide, glass fibers, glass beads or mineral fibers. In another preferred embodiment, the additives serve to further modify the polyamide powders of the invention, for example for pigmentation or for optimizing the mechanical properties of the coating or test specimen produced with the polyamide powder. One additive or a mixture of two or more additives may be present in the composition of the invention. In another preferred embodiment of the composition of the invention, the amount of the additive present is from 0 to 4.99% by weight, more preferably from 0 to 2.99% by weight, in particular from 0 to 0.99% by weight, more preferably from 0 to 0.49% by weight, in particular from 0 to 0.249% by weight, and particularly preferably from 0 to 0.19% by weight. In another preferred embodiment the amount of the additive present is from 0 to 0.17% by weight, in particular from 0 to 0.14% by weight, more preferably from 0 to 0.11% by weight, and particularly preferably from 0 to 0.09% by weight.

The change in the flow time of polyamide powders after storage indicates whether the flowability of the powders has changed as a result of storage. If the flowability of the polyamide powders has been reduced due to storage as a consequence of, for example, temperature variations and humidity variations, the flow time will increase. The storage of polyamide powders subject to temperature variations and humidity variations can be simulated in the laboratory and the flow time can be determined to DIN 53492.

After conditioning at 95% relative humidity (6 days, 40° C.) followed by conditioning at 50% relative humidity (24 hours, 20° C.) the polyamide powders of the invention exhibit an increase in flow time, determined to DIN 53492, of less than 20%. In another preferred embodiment, the increase in the flow time is less than 10%, more preferably less than 5%.

The drying loss from the flow aids of the invention can be determined by ISO 787/2. Using this procedure, the flow aid is conditioned for 5 days at a relative humidity of 95%. It is preferable for the conditioning to be carried out at 20° C. and at atmospheric pressure. After 5 days of conditioning, the drying loss of the flow aid is determined to ISO 787/2 by heating to 105° C. for 2 hours. The drying loss is given as change in the weight of the flow aid in percent. The drying loss is preferably less than 0.8%, particularly preferably less than 0.6%, more preferably less than 0.5%, and still more preferably less than 0.4%.

In principal, all types of mixers are suitable for producing the polyamide powder of the invention. The mixing time is preferably less than 120 minutes, more preferably less than 90 minutes. In one preferred embodiment, the polyamide powder and the flow aid are mixed in a high-speed mixer. Use may be made of any high-speed mixer which can exert a high level of shear during the mixing process. The mixing time is less than 10 minutes. The mixing time is preferably less than 5 minutes. The advantage of this preferred embodiment is intimate and homogeneous mixing of polyamide powder and flow aid without forcing the flow aid into the grains of polyamide.

The composition of the invention may be used in processes for coating moldings. The moldings may be composed of or contain metal or a metal alloy. In the coating process, the composition can be fluidized by injecting a gas during the coating procedure. As an alternative, the composition of the invention may be atomized by means of a spray gun. Suitable coating processes include fluidized-bed sintering, rotational sintering, electrostatic coating, tribocoating, or a minicoat process. Since the composition of the invention has good flow and does not cake, homogeneous layers form on the moldings.

Surprisingly, when the composition of the invention is used in a fluidized-bed sintering process no cratering is found on the resultant polyamide surface. Without providing a theoretical basis for this phenomenon, one explanation is that by absorbing little or no water the flow aids of the invention are unlike the flow aids of the prior art. During the coating procedure, no water vaporizes from the applied layer thus avoiding cratering.

When a laser-sintering process is used to build up test specimens, powders are applied in layers and each is fused after exposure to laser light to give a homogeneous solid. Agglomerates in the powder and/or inadequate powder flowability can lead to non uniform powder layers in the respective plane within the structure, and cause cavities on the finished component, and also defects at the edges and surfaces. When an agglomerate-free powder with consistently good flowability is used, only a few, or small, cavities form in the test specimen during laser-sintering, a particular result being an improvement in the mechanical properties of the component. At the same time, the number of defects on the surface and edges is minimized. A homogeneous surface is formed on the test specimen. The composition of the invention was also found to give improved quality of the test specimens produced by the laser-sintering process. Because the composition has consistent flowability, there is no undesirable caking and therefore there are no major cavities in the composition.

The composition of the invention may also be used for producing cosmetics. It has been found that the consistently good flowability exhibited by the powders leads to very homogeneous mixing of the individual constituents of the cosmetics. In prior art compositions, caking is present after storage at varying temperature and humidity, and when the material is used to produce cosmetics the cosmetics have agglomerates which adversely affect their quality.

The composition of the invention may also be used to produce coating materials. As with cosmetics, a requirement with coating materials is that the quality of the individual components is independent of the storage conditions. The coating materials have no agglomerates which cause undesirable marking, matting, or roughening of the surface of the coating material applied.

The examples below are intended to provide an illustration of the present invention, but are not intended to further limit or restrict the invention as claimed in the appended claims.

EXAMPLES

Example 1

The flow aids of the invention Aerosil® R 812 and Aerosil® R 972, and the comparative example Aerosil® 200 are conditioned for 5 days at a temperature of 20° C. and a relative humidity of 95%. The drying loss to ISO 787/2 is then determined after storage for 2 hours at 105° C. The drying loss is given as change in weight of the flow aids in percent as a result of drying.

TABLE 1

| Flow aid | drying loss [%] | Comments |
| --- | --- | --- |
| Aerosil ® R 812* | <0.1 | No caking |
| Aerosil ® R 972* | <0.1 | No caking |
| Aerosil ® 200* (Comparative example) | 18.8 | Caked powder |

*Aerosil ® is a registered trademark of Degussa AG

The drying losses (table 1) measured reflect the fact that the flow aids Aerosil® R 812 and Aerosil® R 972 absorb no water (drying loss less than <0.1%) during storage in an environment with high relative humidity, and do not cake. When the comparative example Aerosil® 200 is stored in an environment with very high humidity it absorbs so much water that the powder, which was previously flowable, cakes.

Example 2

5 g (0.25 part) of Aerosil® R 812 are mixed for 5 minutes with 2 kg (100 parts) of nylon-12 powder produced as in U.S. Pat. No. 4,4334,056 (incorporated herein by reference in its entirety) with a median particle diameter $d_{50}$ of 98 μm (laser scattering) and a bulk density to DIN 53466 of 480 g/l, using the dry-blend process and a Henschel P10 mixer at 400 rpm. The flowability of the resultant composition is determined to DIN 53492 immediately after the mixing process. After conditioning for 6 days at 40° C. and 95% rel. humidity, followed by conditioning of the composition for 24 hours at 20° C. and 50% rel. humidity, the flowability is determined again. The flowability of the composition prior to and after conditioning is found by determining the flow time in seconds for 150 g of composition to DIN 53492. The flow time is given in table 2.

Example 3

2 kg (100 parts) of nylon-12 powder from example 2 and 5 g (0.25 part) of Aerosil® R 972 are mixed as in example 2. The flowability of the composition is determined as described in example 2 and is listed in table 2.

Example 4

2 kg (100 parts) of nylon-12 powder from example 2 and 0.5 g (0.025 part) of Aerosil® R 812 are mixed as in example 2. The flowability of the composition is determined as described in example 2 and is listed in table 2.

Example 5

2 kg (100 parts) of nylon-12 powder from example 2 and 0.3 g (0.015 part) of Aerosil® R 812 are mixed as in example 2. The flowability of the composition is determined as described in example 2 and is listed in table 2.

Example 6

2 kg (100 parts) of nylon-12 powder from example 2 and 5 g (0.25 part) Aerosil® 200 are mixed as in example 2. The flowability of the composition obtained is determined as described in example 2 and is listed in table 2.

TABLE 2

| Composition | Flow time after mixing | Flow time after conditioning at high humidity | Percentage change in flow time as a result of conditioning at high humidity |
|---|---|---|---|
| Composition from example 2 | 12.8 s | 13.2 s | +3% |
| Composition from example 3 | 13.1 s | 14.2 s | +8% |
| Composition from example 4 | 13.4 s | 13.9 s | +4% |
| Composition from example 5 | 15.6 s | 17.2 s | +10% |
| Composition from example 6 (comparison) | 12.6 s | 18.1 s | +44% |

The flow time for the composition was determined for 150 g of the composition to DIN 53492.

The compositions of the invention from examples 2 to 5 show no significant change in flowability after conditioning for 6 days in a chamber at controlled temperature and humidity, at 40° C. and a relative humidity of 95%, followed by conditioning for 24 hours at 20° C. and 50% rel. humidity. The increase in flow time is from 3% to 10%. The consistently good flowability irrespective of the storage conditions for the compositions from examples 2 to 5 means that the processability of the compositions is unimpaired. The flowability of comparative example 6 in the freshly mixed state is comparable with examples 2 to 5 of the invention. However, comparative example 6 shows a significant increase in the flow time by 44%, and therefore significantly poorer flowability, after conditioning for 6 days in a chamber with controlled temperature and humidity at 40° C. and 95% relative humidity, followed by conditioning for 24 hours at 20° C. and 50% rel. humidity. This poorer flowability led to processing difficulties and quality problems in the products produced using this composition.

German application 10251790.8 is incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

The invention claimed is:

1. A composition comprising, by weight of the composition, of from 88 to 99.99% of a polymer component selected from the group consisting of nylon-12, nylon-11, nylon-6, 10, nylon 6,12, nylon-10,12, nylon-6,6, and mixtures thereof, which polymer component is the sole polymer component in the composition, and from 0.01 to 0.25% of a flow aid selected from the group consisting of a hydrophobicized silica, a hydrophobic silica, and mixtures thereof, wherein the drying loss of the flow aid after 5 days of conditioning at relative humidity of 95% is less than or equal to 1% by weight.

2. The composition as claimed in claim 1, wherein the polymer component has a median particle size of from 0.1 to 250 µm.

3. The composition as claimed in claim 1, wherein the flow aid has a median particle size of from 10 nm to 150 µm.

4. The composition as claimed in claim 1, wherein the flow aid has a specific surface area of from 20 to 600 m²/g.

5. The composition as claimed in claim 1, wherein the increase in the flow time of the composition after six days of conditioning at 95% relative humidity and 40° C. followed by 24 hours of conditioning at 50% relative humidity at 20° C. is less than 20%.

6. The composition as claimed in claim 1, wherein the flow aid is present in an amount effective for preventing caking.

7. The composition as claimed in claim 1, wherein the flow aid is present in an amount effective for preventing an increase in the flow time of the polymer component of greater than 5% after exposure to an atmosphere of 95% relative humidity at 40° C. for 6 days followed by exposure to an atmosphere of 50% relative humidity at 20° C. for 24 hours.

8. The composition as claimed in claim 7 wherein the increase in flow time is greater than 10%.

9. A process for coating a molding, comprising coating the molding with a composition as claimed in claim 1.

10. The process as claimed in claim 9, wherein the molding comprises a metal or a metal alloy.

11. The process as claimed in claim 9, wherein the composition is fluidized during coating by injection of a gas.

12. The process as claimed in claim 9, wherein the coating is fluidized-bed sintering, rotational sintering, electrostatic coating, tribocoating or minicoat processing.

13. A process for producing a sintered amide, comprising sintering the composition as claimed in claim 1 by laser-sintering to form the article.

14. A cosmetic comprising the composition claimed in claim 1.

15. A coating material comprising the composition claimed in claim 1.

16. The composition as claimed in claim 1, wherein the polymer component is present in an amount of 95 to 99.99% by weight.

17. The composition as claimed in claim 1, wherein the polymer component is present in an amount of 99 to 99.99% by weight.

18. The composition as claimed in claim 1, wherein the polymer component is present in an amount of 99.8 to 99.99% by weight.

19. The composition as claimed in claim 1, wherein the polymer component is present in an amount of 99.88 to 99.99% by weight.

20. The composition as claimed in claim 1, wherein the polymer component is present in an amount of 99.9 to 99.99% by weight.

* * * * *